United States Patent [19]

Laplanche

[11] Patent Number: 4,643,729
[45] Date of Patent: Feb. 17, 1987

[54] ELASTIC FASTENERS FOR A DIAPER

[75] Inventor: Pierre Laplanche, Turckheim, France

[73] Assignee: Beghin-Say S.A., Thumeries, France

[21] Appl. No.: 734,609

[22] Filed: May 16, 1985

Related U.S. Application Data

[63] Continuation of Ser. No. 355,570, filed as PCT FR81/00067, Jun. 2, 1981, published as WO81/03601, Dec 24, 1981 abandoned.

[30] Foreign Application Priority Data

Jun. 19, 1980 [FR] France .............................. 80 13577

[51] Int. Cl.⁴ .............................................. A61F 13/16
[52] U.S. Cl. ..................................... 604/389; 604/390
[58] Field of Search ................................ 604/389, 390

[56] References Cited

U.S. PATENT DOCUMENTS

| | | | |
|---|---|---|---|
| 3,800,796 | 4/1974 | Jacob | 604/390 |
| 3,869,761 | 3/1975 | Schaar | 604/390 |
| 3,920,018 | 11/1975 | Schaar | 604/392 |
| 3,952,744 | 4/1976 | Aldinger | 604/390 |
| 4,074,716 | 2/1978 | Schaar | 604/390 |
| 4,100,921 | 7/1978 | Schaar | 604/390 |
| 4,389,212 | 6/1983 | Tritsch | 604/389 |

*Primary Examiner*—C. Fred Rosenbaum
*Assistant Examiner*—Sherri E. Vinyard
*Attorney, Agent, or Firm*—A. W. Breiner

[57] ABSTRACT

An elastic fastener for diapers.

It comprises an extensible central part and two non-stretching lateral parts. The two lateral parts are integral with a support band provided with a precut line which will be ruptured at the time of use.

Fastening clothing, underwear, in particular infant's diapers.

9 Claims, 8 Drawing Figures

4,643,729

ELASTIC FASTENERS FOR A DIAPER

06/355,570 filed as PCT FR81/00067, Jun. 2, 1981, published as WO81/03601, Dec. 24, 1981 now abandoned.

TECHNICAL AREA

The present invention concerns an elastic fastener to be used in particular in a fastening system tying together the fore and rear parts of a disposable infant diaper.

The invention also relates to a manufacturing process for such a fastener on a production machine for disposable diapers.

The disposable infant diapers consist of an absorbing mass in the form of a pad of cellulose fibers placed between an impermeable support sheet and a foil permeable to liquids called the non-woven sheet which will be in contact with the infant's skin.

PRIOR ART

Adhesive fasteners are used to maintain the diaper around the infant's waist, one end of said fasteners being fixed to the impermeable support sheet while the other end, which is coated with an adhesive protected by a siliconized paper, is free. When the diaper is being put to use, the siliconized paper is removed, and the bared adhesive part is applied to the upper rear part of the impermeable support sheet.

To prevent joining too tightly the fore and rear parts of the diaper, the attempt has been made to make the fasteners elastic.

The French Pat. No. 72 17105 describes a semi-elastic fastening band with a central segment which can freely extend and two non-stretching end segments, one of the end segments being fixed to a lateral edge of the diaper at the infant's waist while the other end segment is free and comprises a surface with a pressure-applied adhesive.

Again an elastic fastener is known from the U.S. Pat. No. 3,920,018 which consists of an extensible loop or a fastener folded into a C.

When the diapers are being manufactured, the fasteners are in part outside the surface defined by the diapers, which prevents high output rates. Moreover, in the special case of the extensible loop fastener, the need to insert the finger into the ill-formed loop complicates the opening action exerted on the fastener.

Accordingly, a novel fastener structure has been sought which would offer on one hand good elasticity when the diaper is fastened around the infant's waist, and on the other hand some overall rigidity whereby the fastener could be kept in the surface of the diapers during their manufacture, and in general before the fastener would be used.

The French Pat. No. 78 00341 in the name of the applicant describes an elastic fastener folded in the manner of an S, and characterized by comprising a first non-elastic zone, a central elastic zone, and a second non-elastic zone of which the side opposite the central elastic zone is covered with a pressure-sensitive adhesive covered by a protective element itself joined to the central zone by a continuous or discontinuous strip of glue parallel to the folding lines of the fastener.

When this fastener is being used, the free end of the second zone will be pulled, the protective element will detach from this second zone and remain fixed to the elastic zone. Henceforth it is possible to fix the second zone onto the edge of a diaper.

However, this fastener suffers from the drawback that it consists of three distinct elements (a central and two end parts) which thereafter are assembled using adhesives.

The manufacture of such a fastener meets with difficulties when it must be carried out on a high output diaper manufacturing machine.

On the other hand, the protective element of the free end of the fastener is joined to one of the sides of the center elastic part by a bead of glue. Practically, such a junction was found difficult to implement.

DESCRIPTION OF THE INVENTION

The object of the present invention is to create an elastic fastener offering both some rigidity until only the time of use and a simplified structure making possible a high output on the diaper production machine.

To achieve this goal, the two lateral parts of the fastener, which are inelastic, consist of an integral piece in the form of a supporting band provided with a precut line (perforated line), said lateral parts at the time of use being separated at this precut line by pulling on the free lateral part; following this rupture, the two lateral parts remain elastically joined by the central extensible part fixed to both these lateral ones.

The central extensible part can be joined to either or both of the lateral parts by two adhesive tapes located on the same first side of the support band on either side of the precut line.

The second side of the support band is covered with two adhesive tapes to keep both end parts of the fastener on the fore and rear sides, respectively, of the diaper.

Preferably this second side of the support band comprises furthermore a median adhesive tape covering the precut line.

Preferably again the adhesive tapes covering both sides of the support band are arranged in a staggered manner: no point of the support band shall be covered with adhesive on both sides.

In a first embodiment of the invention, the precut line separates the support band into two parts of equal lengths and the fastener is folded into two along a folding line coinciding with the precut line.

In a first variation of the embodiment, the free lateral part is longer than the fixed lateral part and the fastener is folded into two along a folding line located in the free lateral part which is not covered by the central extensible part.

In a second variation of the embodiment, a supplementary part is provided of which the first side acts as the protective band of the free lateral part and of which the second side, which is endowed with an adhesive, permits additional fixing to the edge of the diaper. This supplementary part is preferably fixed to the outside of the diaper edge and allows spreading the tensile force both on the inside and the outside of the diaper edge to which the fastener is fixed.

The manufacturing process for the fastener can be easily implemented for a high output rate using a roll of support bands with widths equal to the desired fastener length.

To make this fastener using a roll of support bands already covered on both sides with the above-mentioned adhesive tapes, it suffices to implement the precut line by any adequate known means, to place longitudinally the extensible band (cross-wise) on the adhesive tapes of the first side of the support bands roll, to fold the structure so obtained along the chosen folding line, next to emplace the protective band (siliconized paper), then cutting the structure so obtained into a series of fasteners which thereafter are fixed to the diapers.

The different variations in embodiments of the fastener can be manufactured by slightly modifying certain stages of this process, as will be shown further below in the text by the description of several embodiments of nonrestricting nature which are the object of this invention and are accompanied by drawings, wherein.

Figure 1:
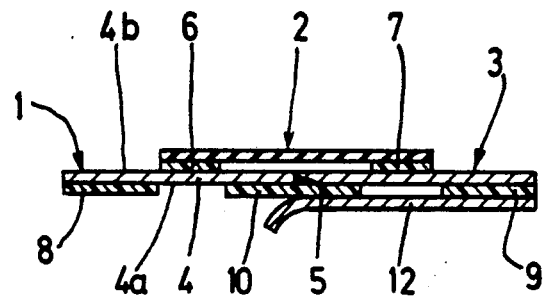
FIG. 1 is a cross-sectional view of the flattened fastener of the invention.
Figure 2:
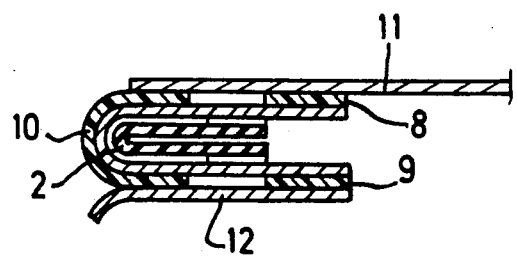
FIG. 2 is a cross-sectional view of the fastener of FIG. 1 when folded and placed on a diaper before being used.
Figure 3:
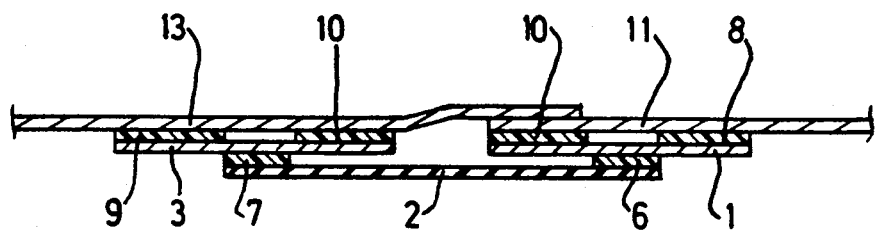
FIG. 3 is a cross-sectional view of the fastener of FIGS. 1 and 2 in its operational position.

The FIGS. 1, 2, and 3 show a first illustrative embodiment of the invention. The fastener comprises three parts: a first lateral part 1, a second extensible central part 2 (extending in the longitudinal fastener direction), and a second lateral part 3.

The two lateral parts 1 and 3 are integral with a support band 4 divided in two by a precut line 5 (a line of perforations for instance) which extends across the entire width of the support band.

The support band 4 may be paper or plastic.

This support band 4 is covered with an adhesive on its two sides 4a and 4b. The adhesive is deposited in strips parallel to the precut line 5.

Two adhesive tapes 6 and 7 are deposited on the side 4b and located on either side of the precut line 5 and of equal widths. These two adhesive tapes make it possible to fix the extensible central part 2 of the fastener consisting of a flat elastic band, a latex, a synthetic rubber, an elastic fabric or any other equivalent elastic material.

The side 4a of the support band 4 is covered with three adhesive tapes 8, 9, and 10 which are preferably arranged in staggered manner with respect to the adhesive tapes 6 and 7 of the side 4b as shown in FIG. 1.

The two adhesive tapes 8 and 9 are arranged at the ends of the support band 4 to act as anchoring for the lateral parts 1 and 3 of the fastener, respectively, on the rear and fore sides of the diaper. Furthermore, a median adhesive tape 10 is provided which covers the precut line and extends on either side of this line on both the lateral parts 1 and 3. The adhesive tapes 8, 9, and 10 which cover the side 4a stretch across zones of the support band which are not covered by the adhesive tapes 6 and 7 of the side 4b; the support band is nowhere covered on both its sides at the same point.

As can be seen in FIG. 2 showing the folded fastener fixed to the diaper before being used, the adhesive tape 8 and the fore part of the median tape located on the lateral part 1 act to anchor the fastener on the diaper (not shown), shown merely by the sheet 11 which belongs to the rear upper side of the diaper.

A protective band 12 (siliconized paper) covers the adhesive tape 9 and that part of the median tape 10 located on the lateral part 3. This protective band prevents any contact with the adhesive of the free lateral part of the fastener before its being used.

Once the fastener has been folded and placed on the diaper (FIG. 2), the fastener is used as follows: the user takes the rim of the protective band 12 covering the free lateral part 3 and the fastener, pulls on all of this free lateral part 3 until the protective band 4 is ruptured along the precut line 5. At this moment the two lateral parts, even though separated, are elastically joined by the extensible central part 2.

While rigid up to the time of use, the fastener due to the rupture of the precut line becomes an elastic fastener making it possible to adjust the fixation around the infant's waist.

The FIG. 3 shows the fastener in the operational position and fixing the rear and fore parts of the diaper (not shown) indicated merely by their ends and, respectively, referenced by 11 and 13.

Figure 4:
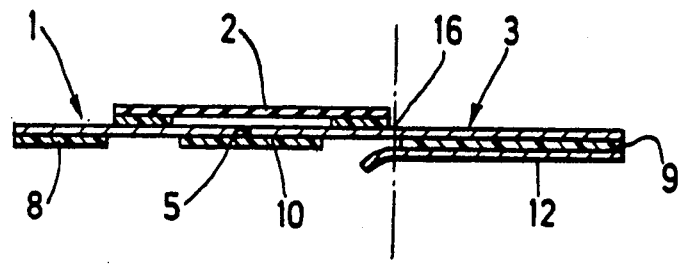
FIG. 4 is a cross-sectional view of the flattened fastener in a first variation of the embodiment of the invention.
Figure 5:
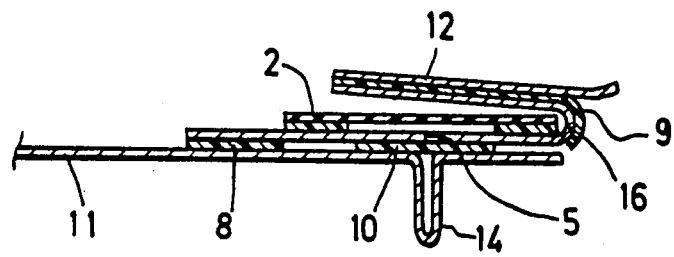
FIG. 5 is a cross-sectional view of the fastener of FIG. 3 when folded and placed on a diaper.

In the embodiment of FIGS. 4 and 5, the precut line 5 no longer is located substantially at the center of the fastener length. Contrary to the previously described embodiment, the free lateral part 3 is longer than the fixed lateral part 1.

The protective band 12 only covers the adhesive tape 9 which is wider than in the previous embodiment.

However, this variation differs from the first embodiment mostly by the folding and the placement of the fastener.

As seen in FIG. 5, the fastener is folded no longer around a line coinciding with the precut line, but around a line referenced as 16 and located on the free lateral part 3 outside the zone of this lateral part covered by the extensible band 2.

In order to allow removing one of these lateral parts with respect to the other at the time of use, the part 11 of the diaper to which the fastener is fixed is provided with a fold 14 which is taken up in part or in whole by the elongation of the extensible part 2.

Figure 6:
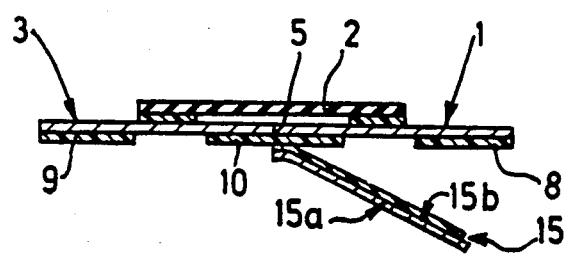
FIG. 6 is a cross-sectional view of the flattened fastener of a second variation in the embodiment of the invention.
Figure 7:
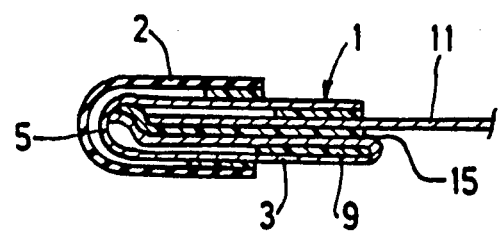
FIG. 7 is a cross-sectional view of the fastener of FIG. 6 when folded and placed on a diaper.
Figure 8:
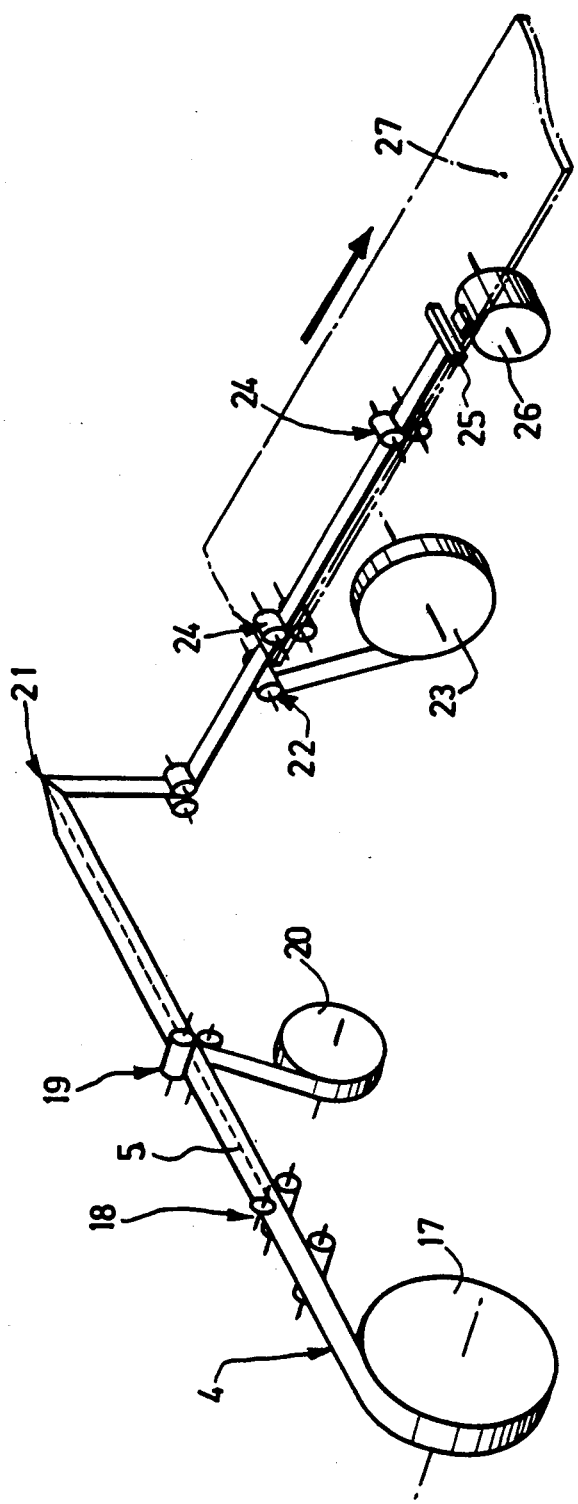
FIG. 8 is a schematic of the various manufacturing stages of a fastener.

A second variation of embodiment is shown in the FIGS. 6 and 7.

The fastener, in addition to the elements already described in relation to the first mode of implementation, also comprises a supplementary part 15 fixed by one of its ends in the vicinity of the precut line 5 on the side of the fixed lateral part 1.

This supplementary part 15 comprises a first side 15a which is siliconized to protect the adhesive of the free lateral part 3, and an adhesive-endowed side 15b to be fixed, like the fixed lateral part, onto the edge 11 of the diaper.

The fastener is folded at the precut line 5 and placed in position as shown in FIG. 7.

The edge 11 of the diaper is "wedged" between the fixed lateral part 1 and the supplementary part 15.

As these two parts 1 and 15 are joined near the precut line (FIG. 6), the tension exerted on the fastener when in use will be spread half over one of the sides of the edge 11 of the diaper and half over the other side.

Such a structure prevents the fastener from slipping on the diaper edge.

The fastener of the FIGS. 1 through 3 is made from a roll of paper or plastic of which the width is equal to the length of the fasteners and already coated with an acrylic adhesive to correspond to the tapes 6 through 10 described above.

Illustratively, the following sizes have been set:

| | | |
|---|---|---|
| fastener length (width of the support band roll) | | 70 mm |
| fastener width | | 30 mm |
| Tape | Width Of The Adhesive Tapes | |
| 6 | 8 mm | |
| 7 | 8 mm | |
| 8 | 13 mm | |
| 9 | 20 mm | |
| 10 | 13 mm | |
| distance between tapes 6 and 7 | | 24 mm. |

The support bands made adhesive in this manner can be provided in the form of rolls 17 several hundred meters long and mounted on the supply drum of the fastener manufacturing apparatus on the diaper production machine.

The support band 4 then is precut at line 18 using a precutting or perforation tool of a common type so as to achieve the precut line 5 of the fasteners. The perforation depth and the distance selected between two perforations, or else the depth of the precut line if it should be continuous, are computed to offer a satisfactory tearing of the support band when put to use.

Next the extensible center part 2 is placed on the adhesive tapes 6 and 7 of one of the sides of the support band roll. This assembly is performed at 19 using simple compression rolls fed on one hand by the support band roll and on the other hand by a lamination roll 20.

Next the assembly is folded at 21 around the precut line using a common technique.

A siliconized protective tape fed from a roll 23 is fixed at 22 on the side corresponding to the free end part of the support band thusly folded.

The structure so obtained then is engaged between the supply rolls 24 which tension it and impart to it a very uniform speed and prevent any slippage.

A counter-knife 25 severs the structure at regular intervals to produce single fasteners which then are attracted by a suction drum 26 after which, following a fraction of a revolution on this suction drum, they are thrown onto the complex of diapers 27 at points corresponding to the fastener fixing zones.

The manufacturing process for the fasteners of FIGS. 4 and 5 is everywhere identical with the one described above except for the transverse position of the precut line and the folding line.

Illustratively, this variation can be illustrated by the following dimensions:

fastener length: 90 mm
length of end part 1: 35 mm
length of end part 3: 55 mm
width of tapes 6 and 7: 8 mm
distance between tapes 6 and 7: 24 mm
width of tape 8: 13 mm
width of tape 10: 20 mm
width of tape 9: 33 mm The manufacturing process for the fasteners of FIGS. 6 and 7 is a variation of the above-described procedure.

In order to manufacture the fastener described in relation to FIGS. 6 and 7, which comprises a supplementary fixing part 15, the folding stage is eliminated and the protective-band emplacement operation is replaced by the assembly of this supplementary part on the support band roll.

The fastener is manufactured and laid flat on the complex of diapers 27.

The fastener will be folded around the edge of the diaper only after having been placed on the complex.

I claim:

1. An elastic fastener adapted to be used for fastening the front and rear faces of a diaper comprising three parts, namely: a first lateral side part fixed on one face of the said diaper, an extensible central part, and a second lateral side part intended to be fastened at the time of use to the other face of said diaper by means of a pressure-sensitive adhesive, characterized in that, before use, the two side parts of the fastener form part of a single piece composed of a support band provided with a transverse precut line, and said lateral parts being separated at the time of use along said precut line by pulling on the said second lateral part with said lateral parts remaining joined together elastically by said extensible central part fastened to each of the said lateral parts by means of two bands of adhesive disposed on one and the same first face of the support band on each side of the precut line, the second face of the support band being coated with adhesive for the fastening of the two side parts of the fastener to the front and rear faces of said diaper, respectively.

2. Fastener according to claim 1 wherein the second side of the support band comprises a median adhesive tape covering the precut line and extending on both of the lateral sides of the fastener.

3. Fastener according to claim 2 wherein said adhesive tapes are fixed to the extensible central part in mutually staggered relation on either side of the support band.

4. Fastener according to claim 1 wherein the precut line is located substantially at mid-length of the support band.

5. Fastener according to claim 1 wherein the precut line is located in such a manner that the second of said two lateral parts is longer than the first of said lateral parts.

6. A continuous manufacturing process for the extensible fasteners of claim 1 starting from support bands, extensible central parts and protective tapes provided in rolls comprising the following stages considered in combinations;
    (a) unwinding the roll of support bands, said support bands having adhesive applied on both faces,
    (b) precutting the unwound support bands along a line parallel to the advance using a precutting tool known per se,
    (c) unwinding the roll of extensible central parts and bonding said parts onto said first face of each precut support bands.
    (d) folding said unwound support band on itself along a folding line coinciding with the precut line or with a line parallel to same, so that the extensible central parts roll shall be located within the fold formed and
    (e) cutting the structure thusly obtained per (d) into a series of fasteners which then are fixed onto diapers.

7. Process according to claim 6 wherein the precut line is the central longitudinal line of the support band roll and the folding line is the precut line.

8. Process according to claim 6 wherein the precut line splits the width of the support band roll into two half bands of unequal widths and the folding line is located in the wider half band at a distance of the precut line such that the folding will not affect the band of extensible central parts.

9. Process according to claim 6 wherein after the folding of the roll of support bands the structure so obtained is affixed to a protective band by means of the adhesive on the second face of said support band of the fastener's free lateral part.

* * * * *